United States Patent
Costa et al.

(10) Patent No.: US 10,525,432 B2
(45) Date of Patent: Jan. 7, 2020

(54) PROCESS FOR THE PREPARATION OF NANOPARTICLES OF NOBLE METALS IN HYDROGEL AND NANOPARTICLES THUS OBTAINED

(71) Applicant: CONSIGLIO NAZIONALE DELLE RICERCHE, Rome (IT)

(72) Inventors: Anna Luisa Costa, Rome (IT); Magda Blosi, Rome (IT)

(73) Assignee: CONSIGLIO NAZIONALE DELLE RICERCHE, Rome (IT)

( * ) Notice: Subject to any disclaimer, the term of this patent is extended or adjusted under 35 U.S.C. 154(b) by 0 days.

(21) Appl. No.: 15/547,662

(22) PCT Filed: Feb. 1, 2016

(86) PCT No.: PCT/IB2016/050501
§ 371 (c)(1),
(2) Date: Jul. 31, 2017

(87) PCT Pub. No.: WO2016/125070
PCT Pub. Date: Aug. 11, 2016

(65) Prior Publication Data
US 2018/0029000 A1 Feb. 1, 2018

(30) Foreign Application Priority Data

Feb. 2, 2015 (IT) .............. MI2015A0130

(51) Int. Cl.
*B01J 13/00* (2006.01)
*A61K 9/06* (2006.01)
*A61K 47/38* (2006.01)
*A61K 33/24* (2019.01)
*A61K 33/28* (2006.01)
(Continued)

(52) U.S. Cl.
CPC .......... *B01J 13/0065* (2013.01); *B01J 23/50* (2013.01); *B01J 23/52* (2013.01); *B01J 23/72* (2013.01); *B01J 31/06* (2013.01); *B01J 35/0013* (2013.01); *B01J 37/036* (2013.01); *B01J 37/04* (2013.01); *C09D 5/14* (2013.01); *C09D 7/67* (2018.01);
(Continued)

(58) Field of Classification Search
None
See application file for complete search history.

(56) References Cited

U.S. PATENT DOCUMENTS

2013/0018112 A1* 1/2013 Thielemans ......... B01J 13/0091
514/781

FOREIGN PATENT DOCUMENTS

WO 2011030170 A1 3/2011
WO 2014078581 A1 5/2014

OTHER PUBLICATIONS

Milovich, "Structure and Dynamics of Catanionic Nanoreservoirs and Functional Hydrogels for Biomedical Applications", Doctoral Seminar, Doctorate School in Chemical and Pharmaceutical Sciences and Technologies of the University of Trieste, Nov. 2013, pp. 1-160. (Year: 2013).*

(Continued)

*Primary Examiner* — Carlos A Azpuru
*Assistant Examiner* — Casey S Hagopian
(74) *Attorney, Agent, or Firm* — King & Schickli, PLLC

(57) ABSTRACT

There is described a versatile and environment-friendly one-pot process for the preparation of nanoparticles of noble metals in hydrogel, obtainable at room temperature using quaternized hydroxyethylcellulose.

11 Claims, 4 Drawing Sheets

(51) Int. Cl.
*A61K 33/34* (2006.01)
*A61K 33/38* (2006.01)
*C09D 7/40* (2018.01)
*B01J 23/50* (2006.01)
*B01J 23/52* (2006.01)
*B01J 23/72* (2006.01)
*B01J 31/06* (2006.01)
*B01J 35/00* (2006.01)
*B01J 37/03* (2006.01)
*B01J 37/04* (2006.01)
*C09D 5/14* (2006.01)

(52) U.S. Cl.
CPC .... *B01J 2231/005* (2013.01); *B01J 2531/005* (2013.01)

(56) References Cited

OTHER PUBLICATIONS

Hebeish Ali et al, "Development of CMC hydrogels loaded with silver nano-particles for medical applications," Carbohydrate Polymers, vol. 92, No. 1, Jan. 2013 (Jan. 2013).
Rodriguez et al, "Influence of cationic cellulose structure on its interactions with sodium dodecylsulfate: implications on the properties of the aqueous dispersions and hydrogels" European Journal of Pharmaceutics and Biopharmaceutics 56 (2003) 133-142.
Cai et al, "Nanoporous Cellulose as Metal Nanoparticles Support," Biomacromolecules 2009, 10, 87-94.
Park et al, "Spatial deformation of nanocellulose hydrogel enhances SERS," BioChip J. (2013) 7(3): 234-241.

\* cited by examiner

PROCESS FOR THE PREPARATION OF NANOPARTICLES OF NOBLE METALS IN HYDROGEL AND NANOPARTICLES THUS OBTAINED

FIELD OF THE INVENTION

The present invention concerns a versatile and environment-friendly one-pot process for the preparation of nanoparticles of noble metals in hydrogel, obtainable at room temperature by using quaternized hydroxyethylcellulose.

STATE OF THE ART

Suspensions of metal nanoparticles are the subject of great scientific interest, due to their versatility in many fields of application.

In particular, silver nanoparticles, by virtue of their chemical-physical characteristics are used in different fields, such as biomedical, optical and electronic devices and as catalysts.

In the biological-medical field, such nanoparticles are studied extensively for their antibacterial and antifungal properties, and in particular it is known that the antibacterial effect increases proportionally to the concentration of the metal, especially for particle sizes below 50 nm. The antimicrobial effect of silver can be exploited on different classes of materials, like for example prostheses, sanitary plastic materials, epidermis, materials for dental use, steel, ceramic tiles, fabrics, as well as in the treatment of water.

Recently, there has been in-depth study of silver nanoparticles for biomedical applications and, for example, interactions of silver nanoparticles with viruses like HIV have been observed, demonstrating the ability to inhibit it. Other studies, moreover, show the ability of nanometric metal to destroy tumour cells.

Other specific applications exploit the optical properties typical of nanometric silver and of other noble metals, characterised by the phenomenon of surface plasmon resonance, like those in surface-enhanced Raman spectroscopy, in optical and sensor devices, in diagnostic medicine and in biological imaging.

Silver nanoparticles are also studied for their catalytic properties, important particularly if synthesised together with other metals or oxides (supported catalysts).

The need of aqueous nanoparticle suspensions of noble metals, stable over time and obtained from biocompatible reactants, represents a challenge to those concerned with synthesis of colloidal nanosuspensions. The requirements imposed for industrial exploitation of the material essentially are:

High concentration, stability over time and control of the dimensions of the nanosols produced, Environmental sustainability and scalability of the process.

The methods proposed in the literature are unable to ensure all of these requirements simultaneously.

Indeed, given the several applications of nanoparticle silver, in the literature it can be seen that the concentrations considered for colloidal systems are, in most cases, very low, usually between 0.001 and 0.005 M, and, in order to control the dimensions, the working conditions are by defect of the reducing agent, thus disadvantageously obtaining partial conversions. The only examples of synthesis with higher concentrations, equal to 0.05-0.06 M with a maximum of 0.2 M, encompass the precipitation of solids or the presence of an excess of stabilizing polymer, so as to form a metal-polymer composite. Moreover, in these studies, reference is rarely made to the stability of the synthesised systems over time, for example, a study concerning the synthesis of nanosols with a concentration of 0.048 M reports a maximum stability of 2 weeks, which is unacceptable.

The use of low concentrations allows to obtain particles of smaller dimensions and more stable, but said concentrations are not suitable for the purposes of an industrial scale up.

In fact, in this regard, it is necessary to consider that the optimisation of a synthesis carried out at a low concentration can be hardly repeated at a higher concentration without incurring problems of stability and aggregation, so that it is important to emphasise that the difficulty presented by industrial scale up exactly consists of finding a method of synthesising colloidal systems that are stable over time, with controlled dimensions and a high concentration.

Another important aspect for the purposes of industrial scale up is certainly the environmental impact and versatility of the synthesis. This makes unsuitable a large number of known syntheses, which exploit microemulsion, hydrothermal methods, syntheses in polymeric matrices, in supercritical fluids, in toxic organic solvents or with reducing agents that are difficult to handle (formaldehyde, hydrazine, hydrides) or with radiolithic methods.

In the same way, also additional stabilizing agents, often polymeric organic compounds (PVP; PVA; PAN, starch) or surfactants (CTAB, SDS; TOAB), should be easy to process and soluble, while avoiding excessive presence thereof with respect to the metal. Indeed, on an industrial scale the solubilisation of the polymers takes a lot of energy and time.

In the synthesis of nanoparticles, moreover, chelating agents are commonly used, since they are capable of being adsorbed on the surface of the particles, limit the growth during the reaction and, limit the coagulation phenomenon by steric effect, thus giving stability to the suspension. Some examples are reported, wherein substances derived from cellulose are used only as stabilizer of the particles, which are reduced in solution by other reactants, or carry out the dual role of stabilizer and reducer, thus leading to good and stable results, but require heating of the reaction environment and in any case yield limited product concentrations (e.g. 0.01 M).

The studies reporting syntheses of metal nanoparticles at room temperature, in water and environment-friendly, hardly have the qualities required of industrial processes: they need biological reduction means (bacteria) or allow the reduction only of metals that are spontaneously very reactive (e.g. gold); frequently, moreover, they produce suspensions at very low concentrations.

In literature, there is a minority of studies describing synthesis methods assisted by microwave heating, also with the addition of reducers and stabilizers considered environment-friendly. However, a conventional heating step with gaseous hydrogen or through microwaves implies a substantial adaptation of industrial plants.

In summary, the most commonly known methods for the production of suspensions of nanoparticles of noble metals exploit the reduction of metal ions from solutions containing salts, as precursors of the metal. The synthesis thus requires a reducing agent, a stabilizing agent and a heating system. Among the reducing agents of natural origin, glucose is most commonly used, which requires the addition of a base to increase its reducing power. In order to obtain a stable system with a homogeneously distributed dispersion of particles, it is however necessary to have a very efficient and uniform heating apparatus. This represents a substantial obstacle to the exploitation and integration of the synthesis of nanoparticles in pre-existing industrial processes, due to:
- the need of a suitably set plant based on the process requirements;
- difficulties in managing variable production volumes;
- energy consumption associated to the management and maintenance of the plant;
- difficulties associated to continuous production of material.

The object of the present invention is therefore to provide a synthesis process of nanoparticles of noble metals capable of overcoming the limitations of known methods, while satisfying the requirements of an industrial scale-up.

SUMMARY OF THE INVENTION

Said object has been achieved by a hydrogel comprising nanoparticles of noble metal, as claimed in claim 1.

For the purposes of the present invention, the terms "metal" and "noble metal" mean Au, Ag, Cu, Pd, and Pt.

In another aspect, the present invention concerns a process for the preparation of said hydrogel.

In another aspect, the present invention concerns a hydrogel comprising said nanoparticles, obtainable by said process.

In a further aspect, the present invention concerns the use of said hydrogel for the release of nanoparticles of noble metal.

BRIEF DESCRIPTION OF THE FIGURES

The characteristics and the advantages of the present invention will become apparent from the following detailed description, from the working Examples provided for illustrative purposes, and from the attached figures, wherein.

DETAILED DESCRIPTION OF THE INVENTION

Figure 1:
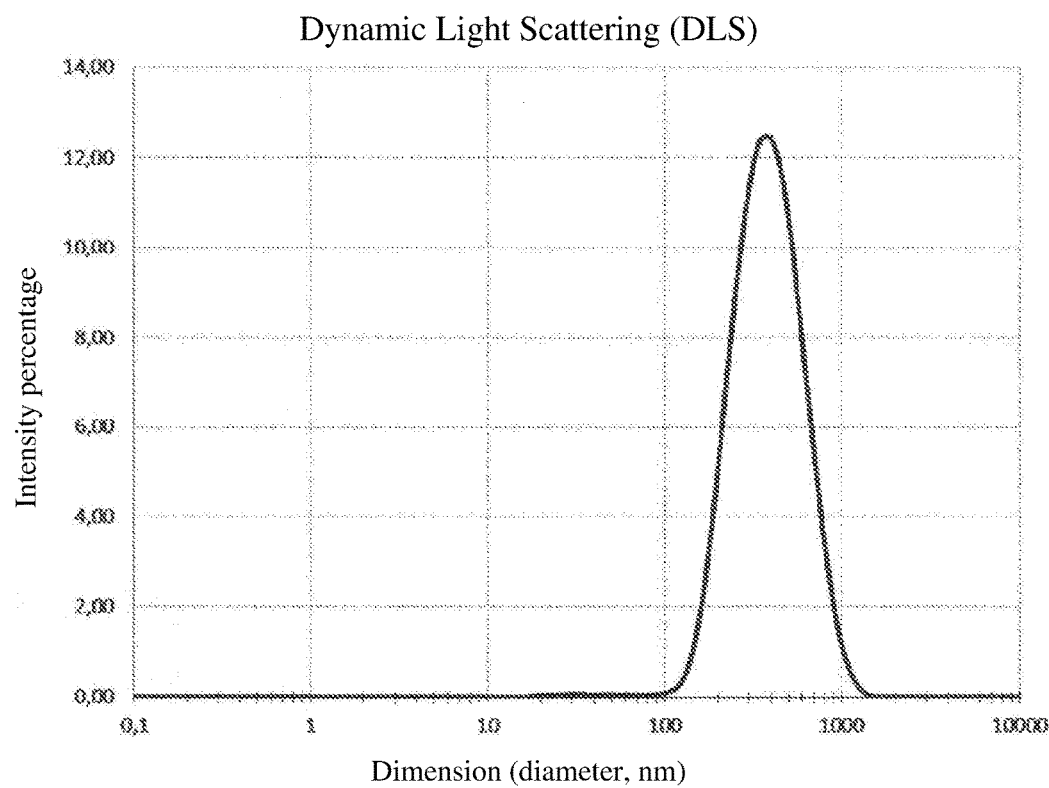
FIG. 1 shows a DLS (Dynamic Light Scattering) analysis of the hydrodynamic diameter of the hydrogel obtained in Example 1.

The invention therefore concerns a hydrogel comprising water, at least one quaternary ammonium salt of hydroxyethylcellulose and nanoparticles of at least one metal, wherein:
- said at least one metal is selected from Au, Ag, Cu, Pd, Pt, and mixtures thereof,
- said at least one quaternary ammonium salt of hydroxyethylcellulose is selected from polyquaternium-4, polyquaternium-10, polyquaternium-24, and polyquaternium-67,
- said nanoparticles of at least one metal have an average particle size distribution $D_{50}$ of 10-100 nm, and are in a concentration of 0.3-5% m/m of the hydrogel.

The average particle size distribution $D_{50}$ is also known as Mass-Median-Diameter (MMD) and is considered the median diameter of the particles on the mass. For the purposes of the present invention, such a parameter is measured through SEM-FEG (scanning electron microscope-field emission guns).

Polyquaternium-4 is the INCI name of the hydroxyethylcellulose dimethyl diallyl ammonium chloride copolymer.

Polyquaternium-10 is the INCI name of a number of quaternary ammonium salts of hydroxyethylcellulose reacted with trimethyl ammonium-substituted epoxide. The solutions of polyquaternium 10 are non-Newtonian and are commercially available (i) in various degrees of viscosity as a function of their molecular weight (they contribute to the viscosity of the formulations) and (ii) with from "high" to "moderate" cationic substitution.

Polyquaternium-24 is the INCI name of the quaternary ammonium salt of hydroxyethylcellulose reacted with dimethyl lauryl ammonium–(average degree of substitution=1) or dimethyl-dodecyl-ammonium-substituted epoxide. This is the hydrophobically modified version of polyquaternium 10. In polyquaternium 24, the degree of substitution with quaternary fat chain is on average equal to one. On the market there is also a number of alkyl dimonium hydroxypropyl oxyethyl cellulose with a greater percentage of grafted cationic fat groups (average degree of substitution of 1.2).

Polyquaternium-67 is the INCI name of the quaternary ammonium salt of hydroxyethylcellulose reacted with a trimethyl ammonium-substituted epoxide and with a lauryl dimethyl ammonium-substituted epoxide.

Polyquaternium 67 is a high viscosity quaternized hydroxyethylcellulose that incorporates variations at the hydrophobic modification and charge level. This family of cationic cellulose polymers combines the trimethyl ammonium function of the polyquaternium 10 with various levels of dimethyl-dodecyl-ammonium hydrophobic function. Their degree of cationic substitution was set at about 0.2, which corresponds to a percentage by weight of nitrogen of about 1%. Low levels of hydrophobic dimethyl-dodecyl-ammonium substitution (HS=0.01) were used to give hydrophobic character to polymers like polyquaternium 10.

In particular, these cationic cellulose polymers are commercially available as UCARE JR 125™, UCARE JR 400™, UCARE JR 30M™, UCARE LR 400™, UCARE LR 30™, SoftCAT SL-5™ [viscosity 2500 mPa·s (1% aq solution); % N 0.8-1.1], SoftCAT SL-30™ [viscosity 2600 mPa·s (1% aq solution); % N 0.8-1.1], SoftCAT SL-60™, SoftCAT SL-100™ [viscosity 2800 mPa·s (1% aq solution); % N 0.8-1.1], SoftCAT SX-400X™ [viscosity 300-500 mPa·s (2% aq solution); % N 2.0-2.2], SoftCAT SX-400H™ [viscosity 300-500 mPa·s (1% aq solution); % N 2.4-2.6], SoftCAT SX-1300H™ [viscosity 800-1800 mPa·s (1% aq solution); % N 2.4-2.6], SoftCAT SX-1300X™ [viscosity 1000-2000 mPa·s (1% aq solution); % N 2.0-2.2], SoftCAT SK-H™, and SoftCAT SK-MH™ (Dow Chemical Company).

Preferably, in the hydrogel of the invention, said at least one quaternary ammonium salt of hydroxyethylcellulose and said metal are in a molar ratio from 1:1 to 10:1.

More preferably, in the hydrogel of the invention, said at least one quaternary ammonium salt of hydroxyethylcellulose and said metal are in a molar ratio from 1.1:1 to 7:1.

In preferred embodiments, said at least one quaternary ammonium salt of hydroxyethylcellulose is polyquaternium-67.

In other preferred embodiments, water is the only solvent present in the hydrogel.

In further embodiments, said at least one quaternary ammonium salt of hydroxyethylcellulose is the only reactant present in the hydrogel since it acts both as a stabilizing agent and as a reducing agent.

In other preferred embodiments, said metal is Ag or Au, with Ag being particularly preferred.

In preferred embodiments, the hydrogel consists essentially of water, at least one quaternary ammonium salt of hydroxyethylcellulose and nanoparticles of at least one metal, wherein:
    said at least one metal is selected from Au, Ag, Cu, Pd, Pt, and mixtures thereof,
    said at least one quaternary ammonium salt of hydroxyethylcellulose is selected from polyquaternium-4, polyquaternium-10, polyquaternium-24, and polyquaternium-67,
    said nanoparticles of at least one metal have an average particle size distribution $D_{50}$ of 10-100 nm, and are in a concentration of 0.3-5% m/m of the hydrogel.

The term "consists essentially of" means that possible further compounds, additives or excipients, if optionally present, do not alter the technical characteristics and the properties of the hydrogel. In particular, said at least one metal and said at least one quaternary ammonium salt of hydroxyethylcellulose are the only active components of the hydrogel.

In other preferred embodiments, the hydrogel consists of water, at least one quaternary ammonium salt of hydroxyethylcellulose and nanoparticles of at least one metal, wherein:
    said at least one metal is selected from Au, Ag, Cu, Pd, Pt, and mixtures thereof,
    said at least one quaternary ammonium salt of hydroxyethylcellulose is selected from polyquaternium-4, polyquaternium-10, polyquaternium-24, and polyquaternium-67,
    said nanoparticles of at least one metal have an average particle size distribution $D_{50}$ of 10-100 nm, and are in a concentration of 0.3-5% m/m of the hydrogel.

Inorganic salts are by-products of the reduction carried out by said at least one quaternary ammonium salt of hydroxyethylcellulose on the precursor of said at least one metal, in the presence of a base, as will be seen more clearly in the description of the preparation process hereinafter.

In another aspect, the present invention concerns a process for the preparation of the hydrogel described above, comprising the steps of:
    a) providing an aqueous solution of an inorganic salt of at least one metal;
    b) providing an aqueous solution of at least one quaternary ammonium salt of hydroxyethylcellulose,
    c) combining the solutions and mixing under stirring at room temperature, and
    d) reacting at room temperature for at least 5 hours, thus obtaining the hydrogel.

The process of the invention has substantial advantages, which make it effectively and conveniently exploitable and integrable even on an industrial scale, upstream of the various application sectors of the noble metals. The main advantages are:
    it is a one-pot process that does not require successive separations, filtrations or purifications; moreover, it is easily integrable at the industrial level since it only needs a batch reactor with a mixer and does not require additional controls;
    the materials used have low environmental impact and are relatively cost-effective;
    the hydrogels thus produced are stable for long periods even at high concentrations of metal nanoparticles;
    the quaternary ammonium salt of hydroxyethylcellulose acts both as a stabilizing agent and as a reducing agent, therefore allowing, both in terms of cost and plant engineering, the use of a single reactant, also advantageously water-soluble;
    no heating is required, thus significantly simplifying the plant and energy requirements;
    the use of water as solvent and the use of "green" reactants ensure the eco-compatibility of the process;
    the dimensions of the nanoparticles of metal are kept below 100 nm with excellent homogeneity; and
    the concentration of metal in the suspensions obtained is greater than those of the methods reported in literature, while offering a high conversion rate, i.e. almost 100%.

The production of nanoparticles of noble metals dispersed in hydrogel matrices is of great industrial interest due to their exploitation in very strategic applications, especially in the field of biomedical engineering. The hydrogel of the invention is even more advantageous if it is considered that the preparations of hydrogel described in literature refer to very complex, multi-step, processes that are difficult to scale up industrially, and which provide for the use of components that are not "green".

Figure 5:
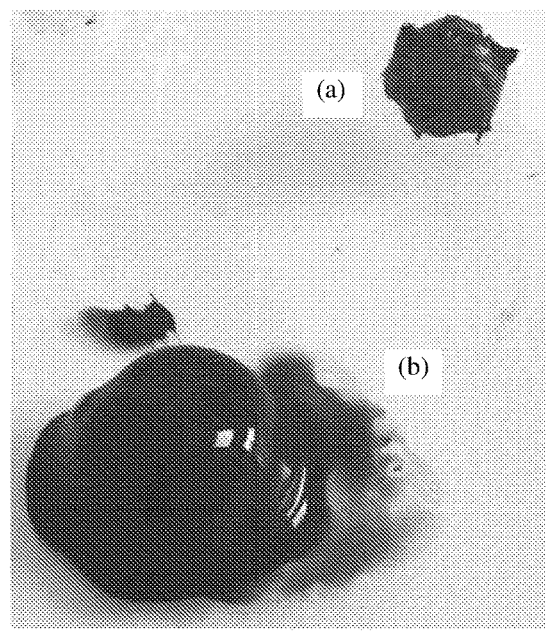
FIG. 5 shows (a) an embodiment of the hydrogel of the invention dried at 80° C. under vacuum, and (b) the same dried hydrogel after immersion in bidistilled water, extraction of the water from the hydrogel by immersion in acetone and subsequent removal of the acetone.

Without wishing to be bound to any theory, it is believed that, upon variation of the pH due to the base, the quaternary ammonium salt of hydroxyethylcellulose reacts thus forming a very viscous gel that slows down the diffusion of the metallic ions; said agent is progressively hydrolysed thus freeing oligosaccharides that are actually responsible for the reduction of the metal. Thus, a synergic process is established, wherein the pH-dependent hydrolysis of the cellulose network simultaneously controls the speed of the nucleation reaction of the nanoparticles and the degree of polymerisation of the final hydrogel. The metal nuclei that progressively form do not succeed in condensing into particles of large dimensions because they are coated by the excess polymer itself, which also performs the role of stabilizer of the hydrogel. The viscosity of the hydrogel can be controlled by acting on the stoichiometric ratios between the reactants used, in particular on the ratio between the base (catalyst) and the cellulose polymer. Once a suitable time has passed, which varies according to the relative concentrations of the reactants, many bonds of the polymer are hydrolysed, thus causing the loss of the high-viscosity gel structure, the suspension has again a low viscosity and shows the characteristic colour of a colloidal suspension of Ag. The hydrogel structure is then stabilized by subjecting the hydrogel to a heat treatment. The hydrogel is, indeed, dried at 80° C. under vacuum for a time ranging from 1 to 3 hours (FIG. 5(a)) and the "swelling" and "de-swelling" capabilities are tested by dipping the dried hydrogel in bidistilled water and then extracting the water by dipping in acetone and subsequent removal of the acetone itself (FIG. 5(b)). As a confirmation of the excellent capabilities of the hydrogel produced to absorb water without redissolving, a "swelling"

ratio equal to 130 is recorded. The amount of water absorbed is easily restored during the "de-swelling" step, once the hydrogel has been removed from the acetone bath.

Preferably, in the process of the invention, said base and said at least one metal are in a molar ratio from 1:1 to 5:1.

More preferably, in the process of the invention, said base and said at least one metal are in a molar ratio from 1.2:1 to 3:1.

Preferably, said inorganic salt of at least one metal is a metal salt of chloride, bromide, iodide, nitrate, sulphate, methyl sulphate, ethyl sulphate, acetate, phosphate, acid sulphate, perchlorate, or mixtures thereof.

More preferably, said inorganic salt of at least one metal is a metal salt of chloride, nitrate, sulphate, or mixtures thereof.

In preferred embodiments, in step c) pH is adjusted to basic pH, preferably between 8 and 12. In this sense, a pH adjuster is added, such as an inorganic base.

Suitable inorganic bases are sodium hydroxide, potassium hydroxide, ammonium hydroxide, sodium carbonate, potassium carbonate, ammonium carbonate, and mixtures thereof. More preferably, said inorganic base is sodium hydroxide.

In preferred embodiments, said at least one quaternary ammonium salt of hydroxyethylcellulose is the only reactant present since it acts both as a stabilizing agent and as a reducing agent.

In a further aspect, the present invention concerns a hydrogel obtainable by the process described above, said hydrogel comprising water, at least one quaternary ammonium salt of hydroxyethylcellulose and nanoparticles of at least one metal, wherein:

said at least one metal is selected from Au, Ag, Cu, Pd, and Pt, said at least one quaternary ammonium salt of hydroxyethylcellulose is selected from polyquaternium-4, polyquaternium-10, polyquaternium-24, and polyquaternium-67, said nanoparticles of at least one metal have an average particle size distribution $D_{50}$ of 10-100 nm, and are in a concentration of 0.3-5% m/m of the hydrogel.

Preferably, in the hydrogel of the invention, said at least one quaternary ammonium salt of hydroxyethylcellulose and said metal are in a molar ratio from 1:1 to 10:1.

More preferably, in the hydrogel of the invention, said at least one quaternary ammonium salt of hydroxyethylcellulose and said metal are in a molar ratio from 1.1:1 to 7:1.

In preferred embodiments, said at least one quaternary ammonium salt of hydroxyethylcellulose is polyquaternium-67.

In other preferred embodiments, water is the only solvent present in the hydrogel.

In further embodiments, said at least one quaternary ammonium salt of hydroxyethylcellulose is the only reactant present in the hydrogel since it acts both as a stabilizing agent and as a reducing agent.

In other preferred embodiments, said metal is Ag or Au, with Ag being particularly preferred.

In another aspect, a kit for the preparation of the hydrogel of the invention is described.

Preferably, said kit comprises:

i) at least one inorganic salt of at least one metal in at least one quaternary ammonium salt of hydroxyethylcellulose, ii) instructions for the preparation of the hydrogel, and optionally iii) an inorganic base in a dedicated container.

It has been surprisingly found that it is possible to provide a kit containing a stable intermediate product i), e.g. in Example 11, formed by at least one inorganic salt of at least one metal in at least one quaternary ammonium salt of hydroxyethylcellulose, to which iii) an inorganic base can be possibly added by an end user, so as to prepare the hydrogel of the invention directly at the moment of use and having the desired viscosity. Indeed, as shown in the following Example 12 and in FIG. 6, it has been demonstrated that the viscosity of the system is adjustable, since it decreases as the concentration of NaOH and the consequent increasing degree of conversion of the reaction from ionic metallic precursor to metal nanoparticles increase. This characteristic allows the stable intermediate product i) to be advantageously stored, handled, and managed in a solid form (absence of inorganic base, maximum viscosity and minimum content of metal nanoparticles), and then to be conveniently used as "in loco" dispenser of metal nanoparticles, once the viscosity has been adjusted by addition of suitable amounts of inorganic base.

Therefore, not only is there the advantage of being able to produce metal nanoparticles directly at the moment of use, an advantage that furthermore makes it easier to pass the strict regulations that the REACH system imposes on those who produce and import nanoparticle systems, but there is also the possibility of having a stable intermediate product i), which can be further modified by addition of inorganic base to obtain the desired viscosity.

Moreover, the present invention concerns the use of the hydrogel as described above for the release of metal nanoparticles, in medical and biomedical applications, in optical devices and as catalysts, and in general in all those applications in which metal nanoparticles are typically used.

In particular, hydrogel can have advantageous application as an active therapeutic agent in coatings for controlling bacterial/mycotic proliferation, in creams and injectable therapeutic substances, or for cicatrizing wounds; as an active component of antibacterial coatings of objects and implants, as a drug-delivery system in medicine and cosmetics; in optical devices (in imaging techniques) and electronic devices (sensors); and as active component of industrial processes, with particular reference to catalysis.

It should be understood that all of the aspects identified as preferred and advantageous for the hydrogel should be considered similarly preferred and advantageous also for the process, and its uses.

All combinations of preferred aspects of hydrogel, of the preparation process, and of its uses, given above, should also be considered to be described.

Hereinafter, non-limiting working examples of the present invention as provided.

EXAMPLES

Example 1

Preparation of 50 ml of a Hydrogel of Silver Nanoparticles (Total Ag Conc. 0.5% m/m)

Two separate solutions are prepared: 0.2 M silver nitrate (8.50 g of salt in 250 ml of water) and 1 M sodium hydroxide (20.0 g of salt in 500 ml of water).

2.45 g of SoftCAT SL-5 are dissolved in 30 ml of water, 12.5 ml of the silver nitrate solution are added and it is stirred; it can be seen that the solution becomes clearer by formation of silver chloride. Then 7 ml of the sodium hydroxide solution is added, mixing carefully, and the solution immediately turns brown and has high viscosity by formation of the gel.

It is reacted for 48 hours obtaining the nanoparticles.

The molar ratios used are as follows: nSoftCAT/nAg=5.5; nNaOH/nAg=2.8.

Figure 2:
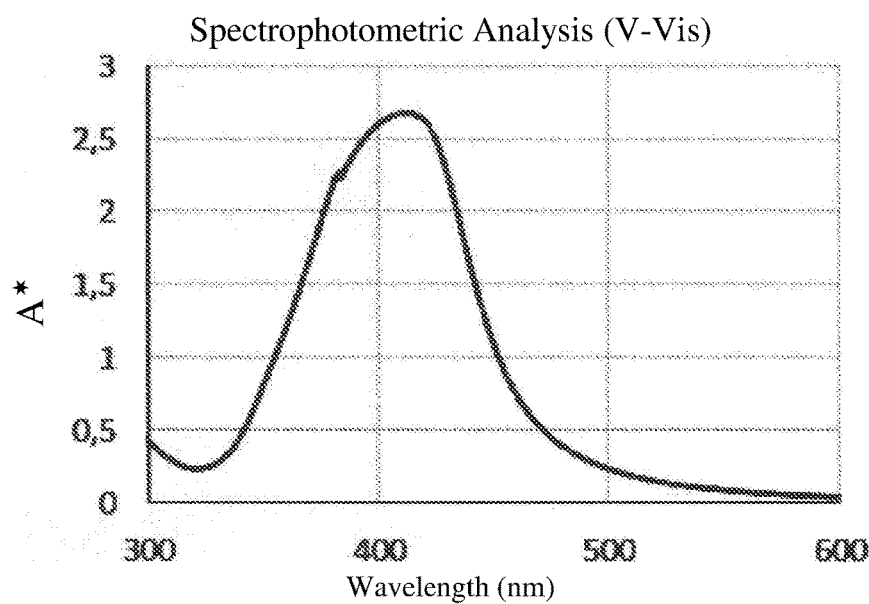
FIG. 2 shows a UV-VIS absorption spectrophotometry analysis, ($\lambda_{max}$: 413 nm) of the hydrogel obtained in Example 1.

Through UV-Vis absorption only one very intense band can be seen with maximum at 413 nm, as shown in FIG. 2.

Figure 3:
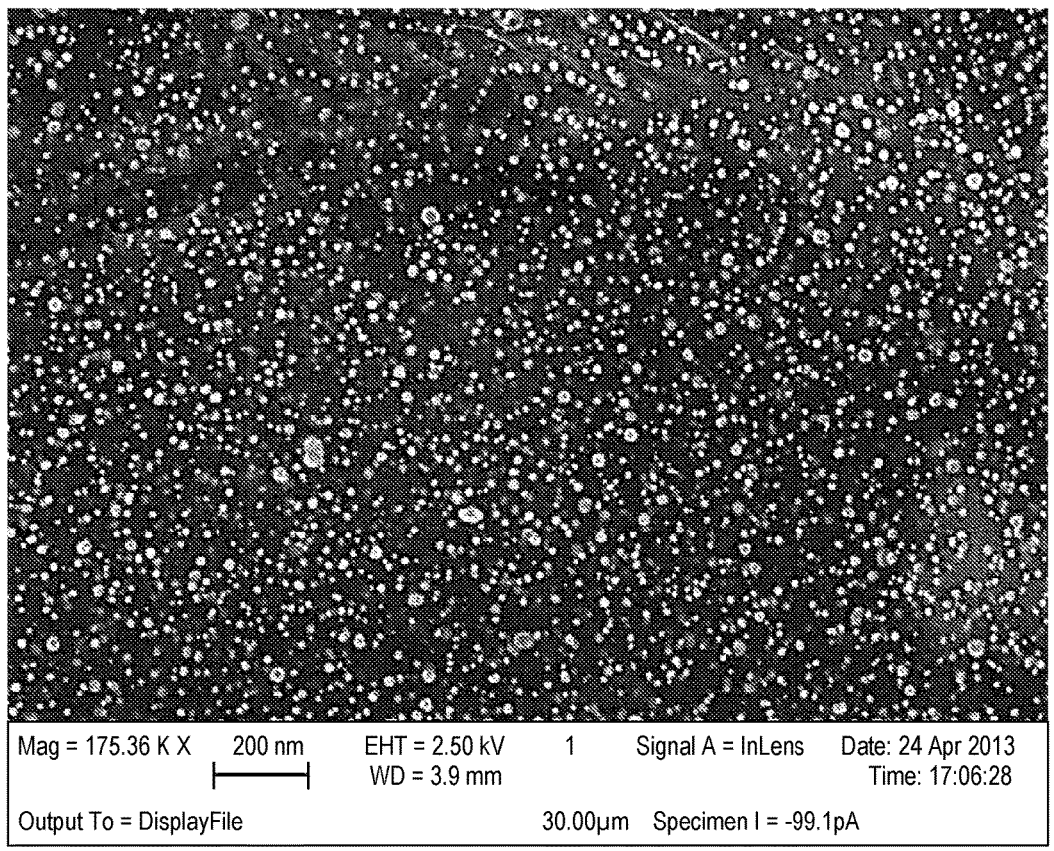
FIG. 3 shows an image recorded through SEM-FEG of the hydrogel obtained in Example 1, and shows an analysis of the distribution of the dimensions of the nanoparticles derived from such an image.
Figure 3:
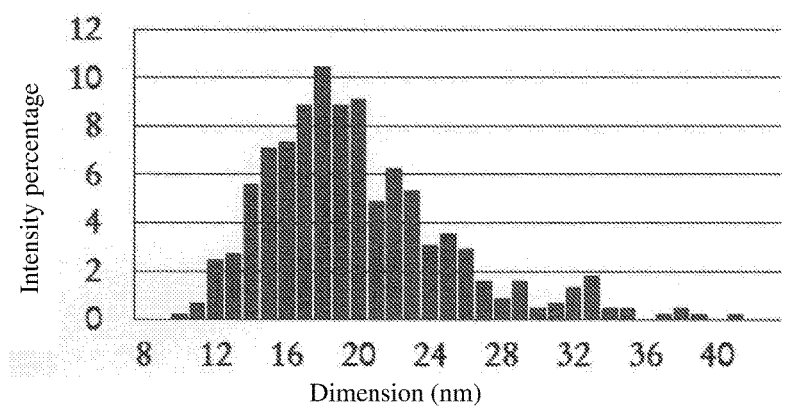

The DLS analysis only recognises the polymeric aggregates (as particles larger than 300 nm), as shown in FIG. 1, but from the SEM-FEG analysis it is possible to confirm the presence of particles and observe the distribution of the dimensions thereof around 20 nm, as shown in FIG. 3.

Such a hydrogel proved to be stable for a period of at least one year (12 months) without producing significant changes in optical properties (UV-Vis) or dimensions (SEM-FEG), indicating that the reaction does not proceed any further.

Figure 4:
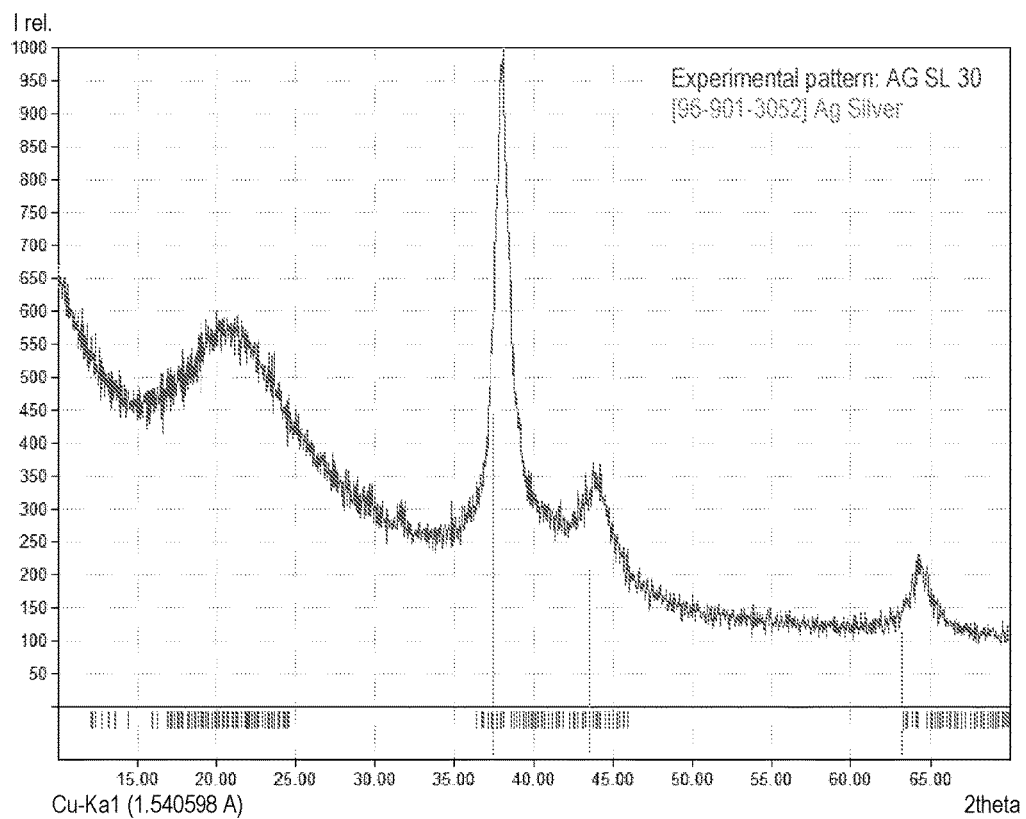
FIG. 4 shows an XRD analysis of the hydrogel obtained in Example 1, suitably dried.

An XRD analysis was also carried out on the suitably dried hydrogel, as shown in FIG. 4, in which it was seen that the metallic Ag phase is present, whereas nitrate and chloride are absent, indicating a total conversion.

Example 2

Preparation of 100 ml of a Hydrogel of Silver Nanoparticles (Total Ag Conc. 1% m/m)

Two separate solutions are prepared: 0.2 M silver nitrate (8.50 g of salt in 250 ml of water) and 1 M sodium hydroxide (20.0 g of salt in 500 ml of water).

4.90 g of SoftCAT SL-5 are dissolved in 22 ml of water, 50 ml of the silver nitrate solution are added and it is stirred; it can be seen that the solution becomes clearer by formation of silver chloride. Then 28 ml of the sodium hydroxide solution is added, mixing carefully, and the solution immediately turns brown and has high viscosity by formation of the gel.

It is reacted for 48 hours obtaining the nanoparticles.

The molar ratios used are as follows: nSoftCAT/nAg=2.75; nNaOH/nAg=2.8.

Through UV-Vis absorption only one very intense band can be seen with maximum at 412 nm.

The DLS analysis only recognises the polymeric aggregates (as particles larger than 600 nm).

Example 3

Preparation of 15 ml of a Hydrogel of Gold Nanoparticles (Total Au Conc. 0.9% m/m)

A 1 M sodium hydroxide solution (20.0 g of salt in 500 ml of water) is prepared.

0.74 g of SoftCAT SL-30 is dissolved in 12.9 ml of water, 2.1 ml of the sodium hydroxide solution is added, mixing carefully; the solution takes on a gelatinous appearance. Then 0.85 g of 30% $AuHCl_4$ solution are added and it is stirred noting that the gel turns red-purple typical of gold nanoparticles of small dimensions.

It is reacted for 48 hours obtaining the nanoparticles.

The molar ratios used are as follows: nSoftCAT/nAu=5.5; nNaOH/nAu=2.8.

Example 4

Preparation of 15 ml of a Hydrogel of Copper Nanoparticles (Total Cu Conc. 0.3% m/m)

A 1 M sodium hydroxide solution (20.0 g of salt in 500 ml of water) is prepared.

0.74 g of SoftCAT SL-30 are dissolved in 12.9 ml of water, 2.1 ml of the sodium hydroxide solution are added, mixing carefully; the solution takes on a gelatinous appearance. Then 0.19 g of copper sulphate are added and it is stirred noting that the gel turns brick red typical of copper nanoparticles.

It is reacted for 48 hours obtaining the nanoparticles.

The molar ratios used are as follows: nSoftCAT/nCu=5.5; nNaOH/nCu=2.8.

Example 5

Preparation of 100 ml of a Hydrogel of Silver Nanoparticles (Total Ag Conc. 2% m/m)

Two separate solutions are prepared: 0.4 M silver nitrate (17.0 g of salt in 250 ml of water) and 1 M sodium hydroxide (20.0 g of salt in 500 ml of water).

4.90 g of SoftCAT SL-5 are dissolved in 44 ml of water, 50 ml of the silver nitrate solution are added and it is stirred; it can be seen that the solution becomes clearer by formation of silver chloride. Then 28 ml of the sodium hydroxide solution are added, mixing carefully, and the solution immediately turns brown and has high viscosity by formation of the gel.

It is reacted for 48 hours obtaining the nanoparticles.

The molar ratios used are as follows: nSoftCAT/nAg=1.38; nNaOH/nAg=1.4

Through UV-Vis absorption only one very intense band can be seen with maximum at 403 nm; with respect to hydrogels at lower concentration this hydrogel tends to remain more aggregated, however a higher intensity absorption peak is recordable.

The DLS analysis only recognises the polymeric aggregates (as particles larger than 100 nm).

Example 6

Preparation of 50 ml of a Hydrogel of Silver Nanoparticles (Total Ag Conc. 0.5% m/m)

Three separate solutions are prepared:
1. 0.2 M silver nitrate (8.50 g of salt in 250 ml of water),
2. 1 M sodium hydroxide (20.0 g of salt in 500 ml of water),
3. SoftCAT SL-5 (2.45 g in 30 ml of water).

As a function of the time passed from the preparation of the third solution, its appearance will be more or less viscous, transparent and colourless; 12.5 ml of the silver nitrate solution are added to this solution and it is stirred vigorously to incorporate the solution in the gel. Then 7 ml of the sodium hydroxide solution are added, mixing vigorously once again; the solution immediately turns brown and has high viscosity by formation of the gel, and if the stirring was not sufficient aggregates of gel that remains transparent and colourless can be seen.

It is reacted for 48 hours obtaining the nanoparticles.

The molar ratios used are as follows: nSoftCAT/nAg=5.5; nNaOH/nAg=2.8.

Through UV-Vis absorption only one not very intense band can be seen with maximum at 412 nm.

The DLS analysis only recognises the polymeric aggregates (as particles larger than 300 nm) and from the SEM-FEG analysis it is possible to confirm the presence of particles and observe the distribution of the dimensions thereof around 20-40 nm.

Example 7

Preparation of 50 ml of a Hydrogel of Silver Nanoparticles (Total Ag Conc. 0.5% m/m)

Two separate solutions are prepared: 0.2 M silver nitrate (8.50 g of salt in 250 ml of water) and 1 M sodium hydroxide (20.0 g of salt in 500 ml of water).

2.45 g of SX-1300H are dissolved in 30 ml of water, 12.5 ml of the silver nitrate solution are added and it is stirred; it can be seen that the solution becomes clearer by formation of silver chloride. Then 7 ml of the sodium hydroxide solution are added, mixing carefully, and the solution maintains the white colour and take on high viscosity by formation of the gel.

The reaction is activated by light radiation, and in this step it is possible to see the browning of the irradiated portions of gel; then it is reacted for 48 hours obtaining the nanoparticles.

The molar ratios used are as follows: nSoftCAT/nAg=5.5; nNaOH/nAg=2.8.

Through UV-Vis absorption only one not very intense band can be seen with maximum at 424 nm. The DLS analysis only recognises the polymeric aggregates (as particles larger than 300 nm).

With respect to hydrogels obtained without irradiation, this hydrogel does not have the expected drop in viscosity.

Example 8

Preparation of 50 ml of a Hydrogel of Silver Nanoparticles (Total Ag Conc. 0.5% m/m)

Two separate solutions are prepared: 0.2 M silver nitrate (8.50 g of salt in 250 ml of water) and 1 M sodium hydroxide (20.0 g of salt in 500 ml of water).

2.45 g of SoftCAT SL-5 are dissolved in 30 ml of water, 12.5 ml of the silver nitrate solution are added and it is stirred; it can be seen that the solution becomes clearer by formation of silver chloride. Then 7 ml of the sodium hydroxide solution are added, mixing carefully, and the solution immediately turns brown and has high viscosity by formation of the gel.

The solution is placed in a thermostatically-controlled bath at 45° C. for 6 hours obtaining the nanoparticles. Then with gentle heating the reaction proceeds faster.

The molar ratios used are as follows: nSoftCAT/nAg=5.5; nNaOH/nAg=2.8.

Through UV-Vis absorption only one very intense band can be seen with maximum at 420 nm.

The DLS analysis only recognises polymeric aggregates larger than 1 μm; from the SEM-FEG analysis it can be seen that there are less particles with respect to the suspensions obtained at room temperature, and the distribution of the dimensions is in the range 20-40 nm.

Example 9

Preparation of 50 ml of a Hydrogel of Silver Nanoparticles (Total Ag Conc. 0.5% m/m)

Two separate solutions are prepared: 0.2 M silver nitrate (8.50 g of salt in 250 ml of water) and 1 M sodium hydroxide (20.0 g of salt in 500 ml of water).

2.45 g of SoftCAT SL-5 are dissolved in 33.5 ml of water, 12.5 ml of the silver nitrate solution are added and it is stirred; it can be seen that the solution becomes clearer by formation of silver chloride. Then 3.5 ml of the sodium hydroxide solution are added, mixing carefully, and the solution immediately turns brown and has high viscosity by formation of the gel.

It is reacted for 48 hours obtaining the nanoparticles.

The molar ratios used are as follows: nSoftCAT/nAg=5.5; nNaOH/nAg=1.4.

Through UV-Vis absorption only one averagely intense band can be seen with maximum at 404 nm.

The DLS analysis only recognises the polymeric aggregates (as particles larger than 500 nm).

Such a hydrogel proved to be stable for a period of at least one year (12 months) without producing significant changes of the optical properties (UV-Vis) or of the dimensions (SEM-FEG), indicating that the reaction does not proceed any further.

With respect to hydrogels obtained with greater amounts of NaOH, this hydrogel has a lower drop in viscosity, producing a final hydrogel having a creamy appearance.

Example 10

Preparation of 50 ml of a Hydrogel of Silver Nanoparticles (Total Ag Conc. 4% m/m)

A 25 M sodium hydroxide solution (100 g of salt in 100 ml of water) is prepared.

34.2 g of SoftCAT SL-30 are weighed in a beaker, 5.9 g of silver nitrate are added, the two compounds are mixed carefully with 46 ml of water, then 4.0 ml of the sodium hydroxide solution are added, mixing carefully for a few minutes, until it has an even brown colour.

It is reacted for 48 hours obtaining the nanoparticles.

The molar ratios used are as follows: nSoftCAT/nAg=5.5; nNaOH/nAg=2.8.

Through UV-Vis absorption only one very intense band can be seen with maximum at 405 nm.

Given the amount of solid substances present in this synthesis, a solid having elastic behaviour is obtained; it is possible to disperse it in water by simple stirring, thus obtaining again hydrogel of nanoparticles at lower concentrations.

Example 11

Preparation of 50 ml of a Stable Intermediate Hydrogel with Reduced Content of Silver Nanoparticles (Total Ag Conc. 0.5% m/m)

A 0.2 M silver nitrate solution (8.50 g of salt in 250 ml of water) is prepared.

2.45 g of SoftCAT SL-5 are dissolved in 30 ml of water, 12.5 ml of the silver nitrate solution are added and it is stirred; it can be seen that the solution becomes clearer by formation of silver chloride.

It is reacted for 7 days obtaining the nanoparticles.

The molar ratios used are as follows: nSoftCAT/nAg=5.5.

Through UV-Vis absorption only one very intense band can be seen with maximum at 413 nm.

The DLS analysis only recognises the polymeric aggregates (as particles larger than 300 nm), but from the SEM-FEG analysis it is possible to confirm the presence of particles and observe the distribution of the dimensions thereof around 20 nm.

Such a hydrogel proved to be stable for a period of at least one year (12 months) without producing significant changes in optical properties (UV-Vis) or dimensions (SEM-FEG), indicating that the reaction does not proceed any further.

Example 12

Preparation of a Kit of Silver Nanoparticles (Total Ag Conc. 0.5% m/m)

The same amounts and the same reactants used in Example 11 are used.

A 0.2 M silver nitrate solution (8.50 g of salt in 250 ml of water) is prepared.

2.45 g of SoftCAT SL-5 are dissolved in 30 ml of water, 12.5 ml of the silver nitrate solution are added; it can be seen that the solution becomes clearer by formation of silver chloride.

A stable intermediate hydrogel product is thus obtained having high viscosity and low content of nanoparticles.

From 0 to 7 ml of a 1 M sodium hydroxide solution (20.0 g of salt in 500 ml of water) are then added, mixing carefully.

Figure 6:
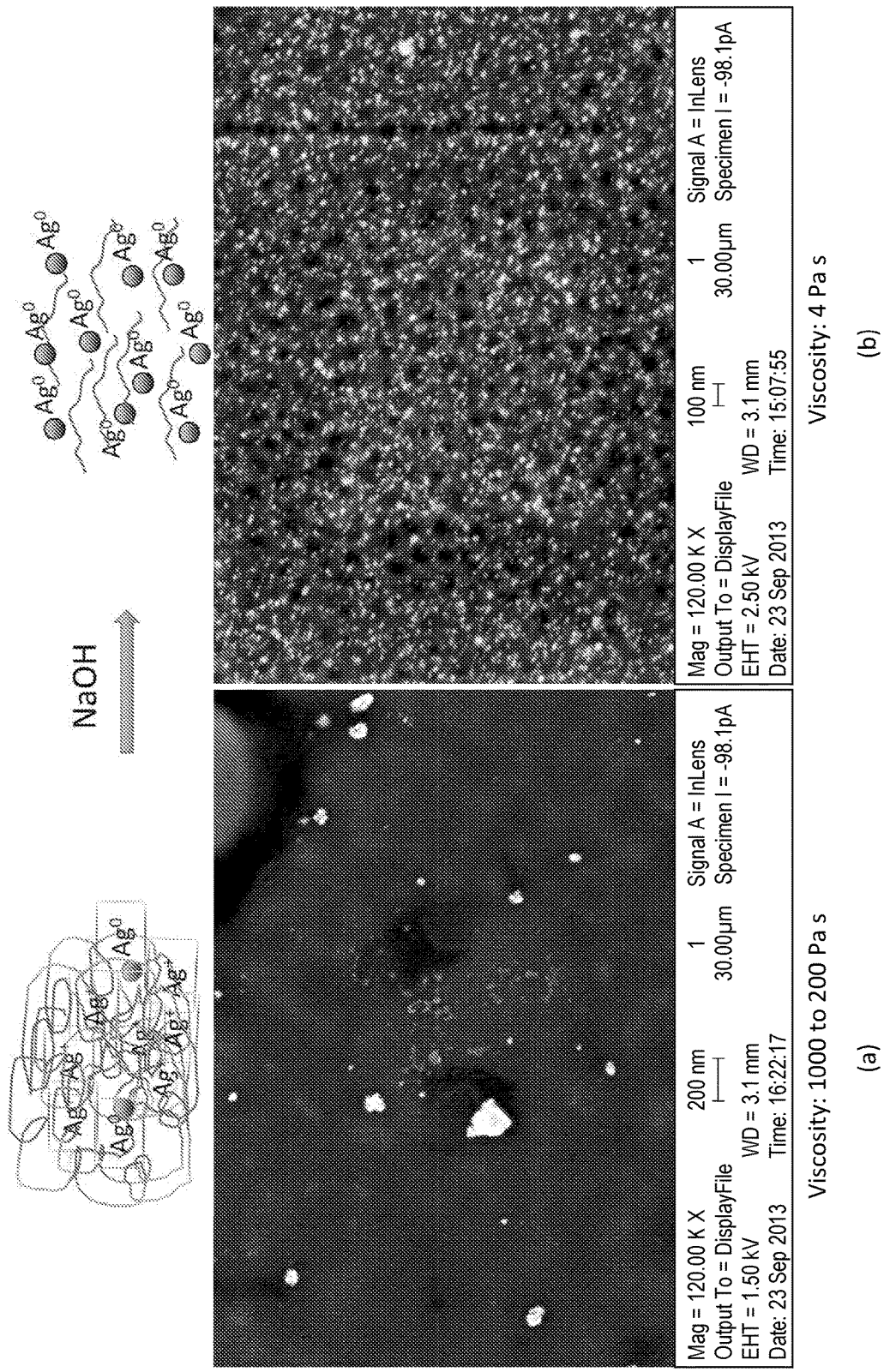
FIG. 6 shows an FEG-SEM analysis of the hydrogel of Example 12 obtained in the absence (a) and in the presence (b) of NaOH and the respective viscosity values measured at 25° C. with a rotational rheometer through cone-plate geometry 4/40 at a deformation speed of 0.1 s$^{-1}$.

With reference to FIG. 6, it is possible to see an FEG-SEM analysis of the hydrogel obtained in the absence (a) and in the presence of 7 ml (b) of NaOH. The viscosity values measured at 25° C. with a rotational rheometer through cone/plate geometry 4/40 at a deformation speed of $0.1\ s^{-1}$ show a progressive decrease in the first 8 hours passing from about 1000 to 200 Pa s and then reaching values of about 4 Pa s after 96 hours. The measurements at the different times were made each time on fresh samples taken from a batch left to rest.

It has been demonstrated that the viscosity and the amount of nanoparticles produced by the system are adjustable, since, as the concentration of NaOH increases, the viscosity decreases and the degree of conversion of the reaction from ionic metallic precursor to metal nanoparticles increases. This characteristic allows the stable intermediate product to be advantageously stocked, handled, and managed in a solid form (absence of inorganic base, maximum viscosity and minimum content of metal nanoparticles), and then to be conveniently used as "in loco" dispenser of metal nanoparticles, once the viscosity has been adjusted by addition of a suitable amount of inorganic base.

The invention claimed is:

1. Hydrogel consisting of water, at least one quaternary ammonium salt of hydroxyethylcellulose, and nanoparticles of at least one metal, wherein:
    said at least one metal is selected from Au, Ag, Cu, Pd, Pt, and mixtures thereof,
    said at least one quaternary ammonium salt of hydroxyethylcellulose is selected from polyquaternium-4, polyquaternium-10, polyquaternium-24 and polyquaternium-67,
    said nanoparticles of at least one metal have an average particle size distribution D50 of 10-100 nm, and are in a concentration of 0.3-5% m/m of the hydrogel.

2. The hydrogel of claim 1, wherein said at least one quaternary ammonium salt of hydroxyethylcellulose and said metal are in a molar ratio from 1:1 to 10:1.

3. The hydrogel of claim 2, wherein said at least one quaternary ammonium salt of hydroxyethylcellulose and said metal are in a molar ratio from 1.1:1 to 7:1.

4. The hydrogel of claim 1, wherein said at least one quaternary ammonium salt of hydroxyethylcellulose is polyquaternium-67.

5. The hydrogel of claim 1, wherein said metal is Ag or Au.

6. Process for the preparation of hydrogel of nanoparticles of at least one metal of claim 1, comprising the steps of:
    a) providing an aqueous solution of an inorganic salt of at least one metal,
    b) providing an aqueous solution of at least one quaternary ammonium salt of hydroxyethylcellulose,
    c) combining the solutions and mixing under stirring at room temperature, and
    d) reacting at room temperature for at least 5 hours, thus obtaining the hydrogel.

7. The process of claim 6, wherein in step c) pH is adjusted to basic pH.

8. The process of claim 7, wherein pH is adjusted by adding an inorganic base, said base and said at least one metal being in a molar ratio from 1:1 to 5:1.

9. Hydrogel obtainable by the process of claim 6, said hydrogel consisting of water, at least one quaternary ammonium salt of hydroxyethylcellulose and nanoparticles of at least one metal, wherein:
    said at least one metal is selected from Au, Ag, Cu, Pd, and Pt,
    said at least one quaternary ammonium salt of hydroxyethylcellulose is selected from polyquaternium-4, polyquaternium-10, polyquaternium-24 and polyquaternium-67,
    said at least metal nanoparticles of at least one metal have a mean particle size distribution D50 of 10-100 nm, and are in a concentration of 0.3-5% m/m of the hydrogel.

10. A medical, biomedical or optical device coated with a coating comprising the hydrogel of claim 1, for use in the release of metal nanoparticles, in medical and biomedical applications, in optical devices and as catalysts.

11. A catalyst comprising the hydrogel of claim 1.

* * * * *